United States Patent
Flores

(10) Patent No.: US 9,618,590 B2
(45) Date of Patent: Apr. 11, 2017

(54) TIP ASSEMBLY FOR MRI-COMPATIBLE MEDICAL DEVICES AND MRI-COMPATIBLE MEDICAL DEVICES INCORPORATING SAME

(71) Applicant: MRI Interventions, Inc., Memphis, TN (US)

(72) Inventor: Jesse Flores, Perris, CA (US)

(73) Assignee: MRI Interventions, Inc., Irvine, CA (US)

( * ) Notice: Subject to any disclaimer, the term of this patent is extended or adjusted under 35 U.S.C. 154(b) by 370 days.

(21) Appl. No.: 14/208,322

(22) Filed: Mar. 13, 2014

(65) Prior Publication Data

US 2014/0275980 A1    Sep. 18, 2014

Related U.S. Application Data

(60) Provisional application No. 61/788,390, filed on Mar. 15, 2013.

(51) Int. Cl.

| A61B 18/18 | (2006.01) |
|---|---|
| G01R 33/28 | (2006.01) |
| A61B 18/14 | (2006.01) |
| A61B 34/20 | (2016.01) |
| A61B 18/00 | (2006.01) |
| A61B 90/00 | (2016.01) |

(52) U.S. Cl.
CPC ........ G01R 33/287 (2013.01); A61B 18/1492 (2013.01); A61B 34/20 (2016.02); *A61B 2018/00351* (2013.01); *A61B 2090/374* (2016.02)

(58) Field of Classification Search
CPC ............... A61B 2034/2051; A61B 2034/2053
See application file for complete search history.

(56) References Cited

U.S. PATENT DOCUMENTS

| 6,701,176 | B1 | 3/2004 | Halperin et al. | |
|---|---|---|---|---|
| 8,369,930 | B2 | 2/2013 | Jenkins et al. | |
| 9,044,156 | B2 * | 6/2015 | Clark | A61B 5/042 |
| 2008/0039709 | A1 | 2/2008 | Karmarkar | |
| 2009/0018497 | A1 * | 1/2009 | Birchard | A61B 5/042 604/95.01 |
| 2009/0171188 | A1 | 7/2009 | Paul et al. | |
| 2010/0168555 | A1 | 7/2010 | Karmarkar et al. | |
| 2010/0317961 | A1 | 12/2010 | Jenkins et al. | |
| 2010/0317962 | A1 * | 12/2010 | Jenkins | A61B 5/055 600/411 |
| 2013/0123598 | A1 | 5/2013 | Jenkins et al. | |
| 2013/0131496 | A1 | 5/2013 | Jenkins et al. | |
| 2014/0187893 | A1 * | 7/2014 | Clark | A61B 5/042 600/373 |

\* cited by examiner

*Primary Examiner* — Long V Le
*Assistant Examiner* — Luther Behringer
(74) *Attorney, Agent, or Firm* — Myers Bigel, P.A.

(57) ABSTRACT

An MRI-compatible tip assembly for an MRI-compatible medical device includes a first tubular member, a second tubular member, a ring electrode, and a tip electrode. The tip electrode proximal end is secured to the first tubular member distal end. The second tubular member distal end is inserted through the ring electrode and is secured to the first tubular member proximal end. When assembled, the tip assembly is a substantially rigid structure. Each tubular member has a recessed portion for a tracking coil.

16 Claims, 8 Drawing Sheets

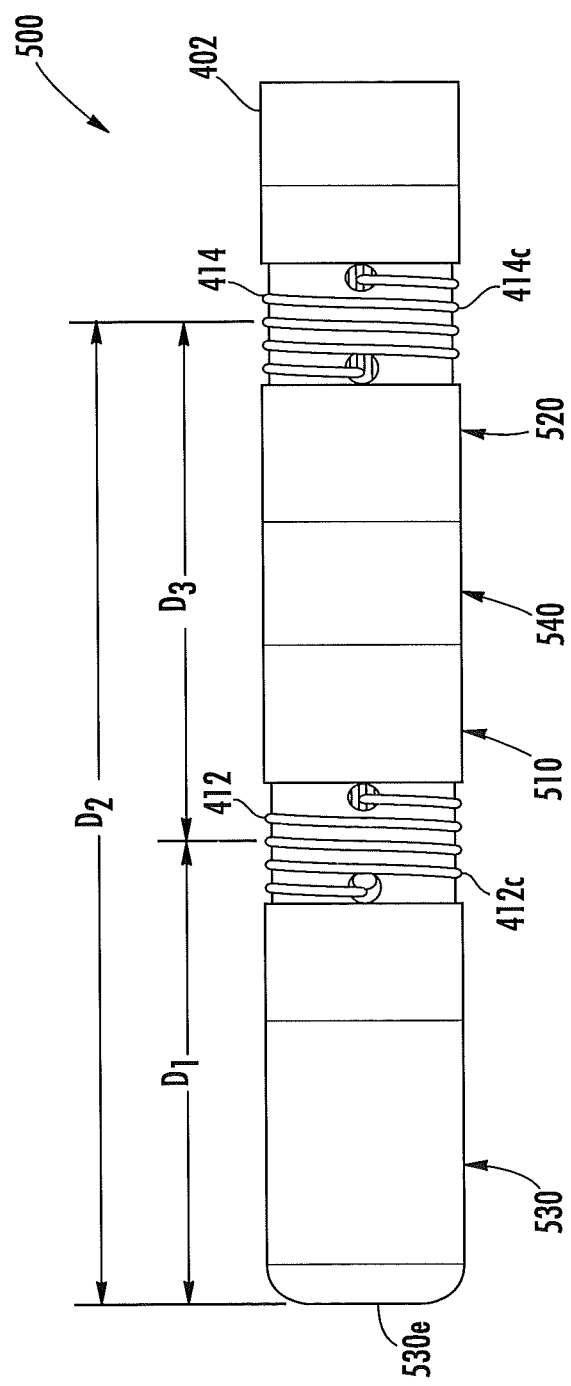

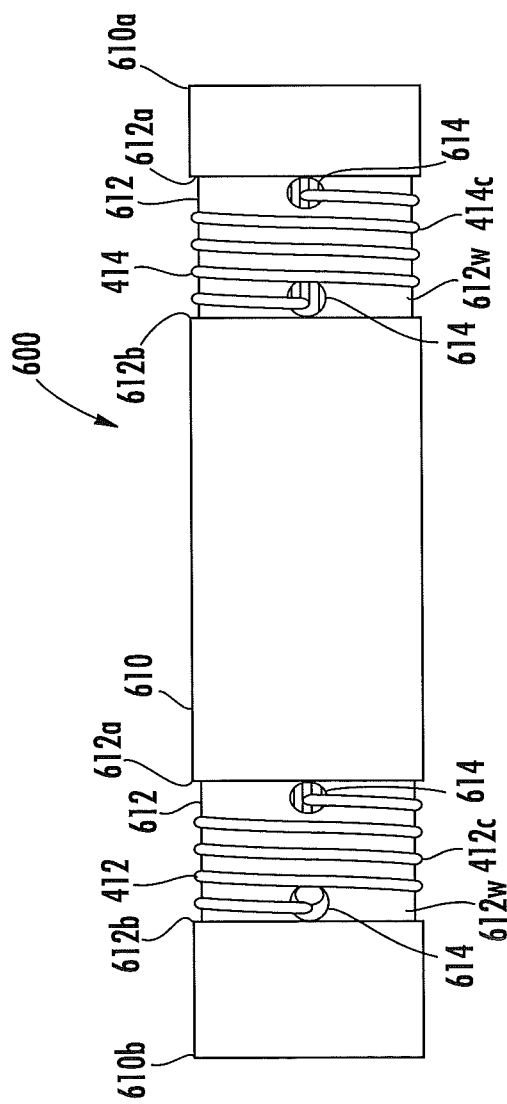

TIP ASSEMBLY FOR MRI-COMPATIBLE MEDICAL DEVICES AND MRI-COMPATIBLE MEDICAL DEVICES INCORPORATING SAME

RELATED APPLICATION

This application claims the benefit of and priority to U.S. Provisional Patent Application No. 61/788,390 filed Mar. 15, 2013, the disclosure of which is incorporated herein by reference as if set forth in its entirety.

FIELD OF THE INVENTION

The present invention relates to MRI-guided systems and may be particularly suitable for MRI-guided cardiac systems such as EP systems for treating Atrial Fibrillation (AFIB).

BACKGROUND

Heart rhythm disorders (arrhythmias) occur when there is a malfunction in the electrical impulses to the heart that coordinate how the heart beats. During arrhythmia, a heart may beat too fast, too slowly or irregularly. Catheter ablation is a widely used therapy for treating arrhythmias and involves threading a catheter through blood vessels of a patient and into the heart. In some embodiments, radio frequency (RF) energy may be applied through the catheter tip to destroy abnormal heart tissue causing the arrhythmia. In other embodiments a catheter tip may be configured to cryogenically ablate heart tissue.

Guiding the placement of a catheter during ablation therapy within the heart is important. Conventional catheter ablation procedures are conducted using X-ray and/or ultrasound imaging technology to facilitate catheter guidance and ablation of heart tissue. Conventional Cardiac EP (Electro-Physiology) Systems are X-ray based systems which use electroanatomical maps. Electroanatomical maps are virtual representations of the heart showing sensed electrical activity. Examples of such systems include the CARTO® brand electroanatomic mapping system from Biosense Webster, Inc., Diamond Bar, Calif., and the ENSITE NAVX® brand system from Endocardial Solutions Inc., St. Paul, Minn.

Magnetic resonance imaging (MRI) has several distinct advantages over X-ray imaging technology, such as excellent soft-tissue contrast, the ability to define any tomographic plane, and the absence of ionizing radiation exposure. In addition, MRI offers several specific advantages that make it especially well suited for guiding various devices used in diagnostic and therapeutic procedures including: 1) real-time interactive imaging, 2) direct visualization of critical anatomic landmarks, 3) direct high resolution imaging, 4) visualization of a device-tissue interface, 5) the ability to actively track device position in three-dimensional space, and 6) elimination of radiation exposure.

Induced RF currents (referred to as RF coupling) on coaxial cables, electrical leads, guide wires, and other elongated devices utilized in MRI environments can be problematic. Such RF coupling may cause significant image artifacts, and may induce undesired RF energy deposition in the tissue in contact/adjacent with the device, resulting in local tissue heating and permanent tissue damage.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, an MRI-compatible tip assembly for an MRI-compatible medical device includes a first tubular member, a second tubular member, a ring electrode, and a tip electrode. Each of the first and second tubular members has opposite proximal and distal ends and a circumferential recessed portion located therebetween. The tip electrode includes opposite proximal and distal ends, and the tip electrode proximal end is secured to the first tubular member distal end. The second tubular member distal end is inserted through the ring electrode and is secured to the first tubular member proximal end. When assembled, the tip assembly is a substantially rigid structure.

In some embodiments, a portion of the tip electrode proximal end is slidably received within the first tubular member distal end to secure the tip electrode to the first tubular member.

In some embodiments, a portion of the second tubular member distal end is slidably received within the first tubular member proximal end.

In some embodiments, the second tubular member distal end has a longitudinally extending slot formed therein. This slot facilitates the connection of one or more conductive leads to the ring electrode.

Each tubular member recessed portion can have opposing ends, and a pair of apertures are formed through walls at each recessed portion with each aperture proximate a respective end of the recessed portion. A first conductor extends outward from one aperture in the first tubular member recessed portion, coils round the first tubular member recessed portion, and extends inward through the other aperture. A second conductor extends outward from one aperture in the second tubular member recessed portion, coils round the second tubular member recessed portion, and extends inward through the other aperture.

In some embodiments, the tip electrode includes an ablation electrode at the distal end. RF power is supplied to the ablation electrode via a conductor through a passageway formed in the tip electrode.

In some embodiments, the tip electrode includes an irrigation passageway formed therein that terminates at a plurality of circumferentially spaced-apart apertures adjacent the tip electrode distal end. A fluid is delivered to the irrigation pathway from a source via a conduit.

In some embodiments, the tip electrode includes a passageway that is configured to house a thermistor for measuring the temperature of tissue proximate to the ablation electrode.

According to embodiments of the present invention, an MRI-compatible medical device includes an elongated flexible shaft having a distal end portion and an opposite proximal end portion, and a substantially rigid tip assembly at the flexible shaft distal end portion. The tip assembly includes a first tubular member, a second tubular member, a ring electrode, and a tip electrode. Each of the first and second tubular members has opposite proximal and distal ends and a circumferential recessed portion located therebetween. The tip electrode includes opposite proximal and distal ends, and the tip electrode proximal end is secured to the first tubular member distal end. The second tubular member distal end is inserted through the ring electrode and is secured to the first tubular member proximal end. When assembled, the tip assembly is a substantially rigid structure.

In some embodiments, a portion of the tip electrode proximal end is inserted within the first tubular member distal end to secure the tip electrode to the first tubular member.

In some embodiments, a portion of the second tubular member distal end is inserted within the first tubular member proximal end.

In some embodiments, the second tubular member distal end has a longitudinally extending slot formed therein. This slot facilitates the connection of one or more conductive leads extending through a lumen in the device shaft to the ring electrode.

Each tubular member recessed portion has opposing ends, and a pair of apertures are formed in each recessed portion with each aperture proximate a respective end of the recessed portion. A first conductor extends outward from one aperture in the first tubular member recessed portion, coils round the first tubular member recessed portion, and extends inward through the other aperture. A second conductor extends outward from one aperture in the second tubular member recessed portion, coils round the second tubular member recessed portion, and extends inward through the other aperture.

In some embodiments, the tip electrode includes an ablation electrode at the distal end. RF power is supplied to the ablation electrode via a conductor extending through a lumen in the device shaft and through a passageway formed in the tip electrode.

In some embodiments, the tip electrode includes an irrigation passageway formed therein that terminates at a plurality of circumferentially spaced-apart apertures adjacent the tip electrode distal end. A fluid is delivered to the irrigation pathway from a source via a conduit extending through a lumen in the device shaft.

In some embodiments, the tip electrode includes a passageway that is configured to house a thermistor for measuring the temperature of tissue proximate to the ablation electrode.

According to some embodiments of the present invention, a tip assembly for an MRI-compatible medical device includes a tubular member having opposite proximal and distal ends and a pair of spaced-apart circumferential recessed portions located between the proximal and distal ends. Each recessed portion has opposing ends. A pair of apertures are formed in each recessed portion with each aperture proximate a respective end of the recessed portion. A first conductor extends outward from one aperture in a first one of the recessed portions, coils round the first recessed portion, and extends inward through the other aperture. A second conductor extends outward from one aperture in the second recessed portion, coils round the second recessed portion, and extends inward through the other aperture.

In some embodiments, a tip electrode is secured to the tubular member distal end. The tip electrode includes opposite proximal and distal ends and the tip electrode proximal end is secured to the tubular member distal end. In some embodiments, a portion of the tip electrode proximal end is slidably received within the tubular member distal end to secure the tip electrode to the tubular member.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate some exemplary embodiments. The drawings and description together serve to fully explain the exemplary embodiments.

FIG. 8 is an enlarged partial plan view of the distal end portion of the ablation catheter of FIG. 5.

FIG. 9 is an enlarged plan view of a tip assembly, according to some embodiments of the present invention.

DETAILED DESCRIPTION

Figure 1:
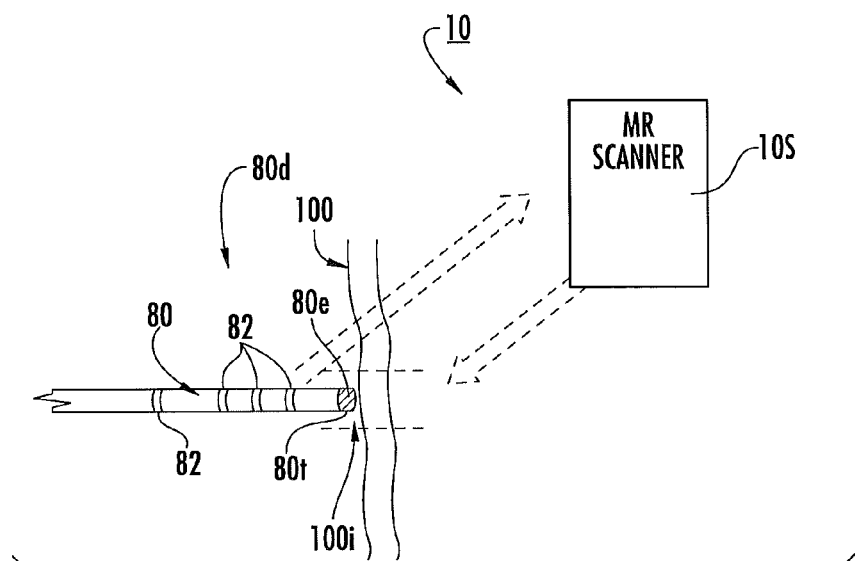
FIG. 1 is a schematic illustration of an MRI-guided system configured to show a device tissue interface using near RT MRI data.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit or flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The term "about", as used herein with respect to a value or number, means that the value or number can vary by +/−twenty percent (20%).

The terms "MRI or MR Scanner" are used interchangeably to refer to a Magnetic Resonance Imaging system and includes the magnet, the operating components, e.g., RF amplifier, gradient amplifiers and operational circuitry including, for example, processors (the latter of which may be held in a control cabinet) that direct the pulse sequences, select the scan planes and obtain MR data. Embodiments of the present invention can be utilized with any MRI Scanner including, but not limited to, GE Healthcare: Signa 1.5 T/3.0 T; Philips Medical Systems: Achieva 1.5 T/3.0 T; Integra 1.5 T; Siemens: MAGNETOM Avanto; MAGNETOM Espree; MAGNETOM Symphony; MAGNETOM Trio; and MAGNETOM Verio.

The term "RF safe" means that the catheter and any (conductive) lead is configured to operate safely when exposed to RF signals, particularly RF signals associated with MRI systems, without inducing unplanned current that inadvertently unduly heats local tissue or interferes with the planned therapy. The term "MRI visible" means that the device is visible, directly or indirectly, in an MRI image. The visibility may be indicated by the increased SNR of the MRI signal proximate the device. The device can act as an MRI receive antenna to collect signal from local tissue and/or the device actually generates MRI signal itself, such as via suitable medical grade hydro-based coatings, fluid (e.g., aqueous fluid) filled channels or lumens. The term "MRI compatible" means that the so-called component(s) is safe for use in an MRI environment and as such is typically made of a non-ferromagnetic MRI compatible material(s) suitable to reside and/or operate in a high magnetic field environment. The term "high-magnetic field" refers to field strengths above about 0.5 T (Tesla), typically above 1.0 T, and more typically between about 1.5 T and 10 T. Embodiments of the invention may be particularly suitable for 1.5 T and/or 3.0 T systems.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., ablation catheter) and the near RT MR image(s) are generated.

The term "intrabody device" is used broadly to refer to any diagnostic or therapeutic medical device including, for example, catheters, needles (e.g., injection, suture, and biopsy), forceps (miniature), knives or other cutting members, ablation or stimulation probes, injection or other fluid delivery cannulas, mapping or optical probes or catheters, sheaths, guidewires, fiberscopes, dilators, scissors, implant material delivery cannulas or barrels, and the like, typically having a size that is between about 5 French to about 12 French, but other sizes may be appropriate.

The term "tracking member", as used herein, includes all types of components that are visible in an MRI image including miniature RF tracking coils, passive markers, and receive antennas. In some embodiments of the present invention a miniature RF tracking coil can be connected to a channel of an MRI Scanner. The MR Scanner can be configured to operate to interleave the data acquisition of the tracking coils with the image data acquisition. The tracking data is acquired in a 'tracking sequence block' which takes about 10 msec (or less). In some embodiments, the tracking sequence block can be executed between each acquisition of image data (the 'imaging sequence block'). So the tracking coil coordinates can be updated immediately before each image acquisition and at the same rate. The tracking sequence can give the coordinates of all tracking coils simultaneously. So, typically, the number of coils used to track a device has substantially no impact on the time required to track them.

MRI has several distinct advantages over X-ray imaging technology, such as: excellent soft-tissue contrast, the ability to define any tomographic plane, and the absence of ionizing radiation exposure. In addition, MRI offers several specific advantages that make it especially well suited for guiding transseptal puncture procedures including: 1) near real-time interactive imaging, 2) direct visualization of critical endocardial anatomic landmarks, 3) direct high resolution imaging of the septum, including the fossa ovalis, 4) visualization of the needle tip-tissue interface, 5) the ability to actively track needle position in three-dimensional space, and 6) elimination of radiation exposure.

Embodiments of the present invention can be configured to guide and/or place diagnostic or interventional devices in an MRI environment (e.g., an interventional medical suite 19, FIG. 3) to any desired internal region of a subject of interest, including, in some embodiments, to a cardiac location. The subject can be animal and/or human subjects.

FIG. 1 illustrates an MRI interventional system 10 with a scanner 10S and a flexible intrabody medical device 80 (e.g., an ablation catheter, mapping catheter, etc.) proximate target tissue 100 at a device-tissue interface 100*i*. The system 10 can be configured to electronically track the 3-D location of the device 80 in the body and identify and/or "know" the location of the tip portion 80*t* of the device 80 (e.g., the ablation tip) in a coordinate system associated with the 3-D imaging space. As shown in FIG. 1, the device 80 can include a plurality of spaced apart tracking members 82 on a distal end portion thereof. In a particular embodiment, the device 80 can be an ablation catheter and the tip 80*t* can include an ablation electrode 80*e* (typically at least one at a distal end portion of the device). Where used, the electrode 80*e* can be both a sensing and ablation electrode.

Figure 2:
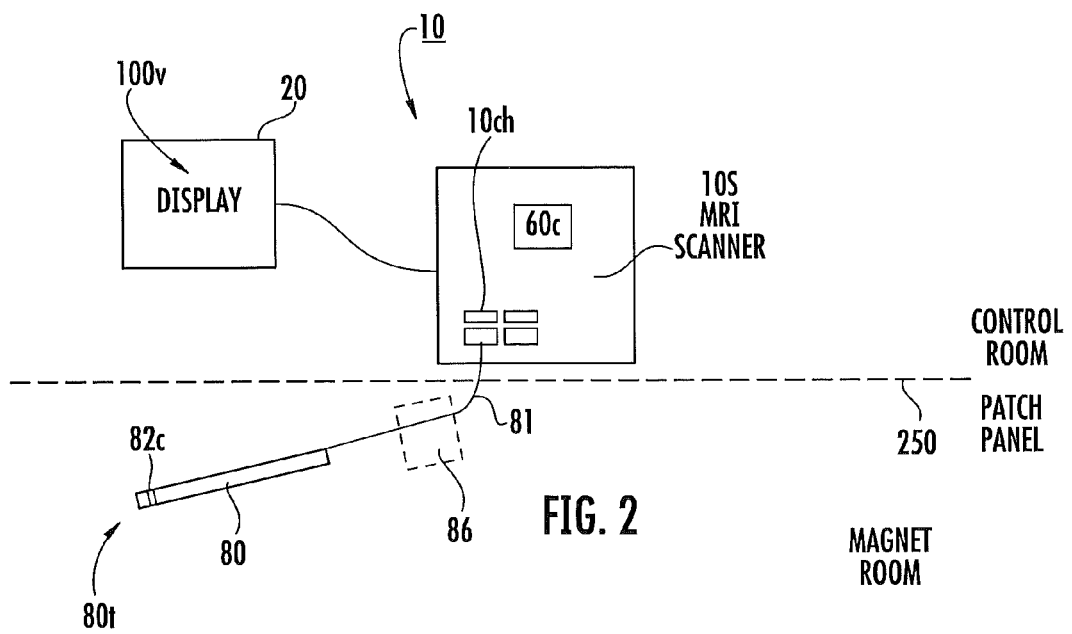
FIG. 2 is a schematic illustration of an intrabody device with a tracking coil electrically connected to a Scanner channel.

The tracking members 82 can comprise miniature tracking coils, passive markers and/or a receive antenna. In a preferred embodiment, the tracking members 82 include at least one miniature tracking coil 82*c* that is connected to a channel 10*ch* of an MRI Scanner 10S (FIG. 2). The MR Scanner 10S can be configured to operate to interleave the data acquisition of the tracking coils 82*c* with the image data acquisition.

Some embodiments of the invention can be utilized with systems that can be used to facilitate ablation of tissue for treating cardiac arrhythmias, or to repair or replace cardiac valves, repair, flush or clean vasculature and/or place stents, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). The cardiac procedures can be carried out from an inside of the heart or from an outside of the heart. The system may also be suitable for delivering a therapeutic agent or carrying out another treatment or diagnostic evaluation for any intrabody location, including, for example, the brain, gastrointestinal system, genourinary system, spine (central canal, the subarachnoid space or other region), vasculature or other intrabody locations. Additional discussion of exemplary target regions can be found at the end of this document.

The system 10 and/or circuit 60*c* (FIGS. 2-3) can calculate the position of the tip 80*t* of the device 80 as well as the shape and orientation of the flexible device based on a priori information on the dimensions and behavior of the device 80 (e.g., for a steerable device, the amount of curvature expected when a certain pull wire extension or retraction exists, distance to tip from different coils 82 and the like). Using the known information of the device 80 and because the tracking signals are spatially associated with the same X, Y, Z coordinate system as the MR image data, the circuit 60*c* can rapidly generate visualizations showing a physical representation of the location of a distal end portion of the device 80 with near RT MR images of the anatomy.

In some embodiments, the tracking signal data is obtained and the associated spatial coordinates are determined while a circuit 60*c* in the MRI Scanner 10S (FIG. 2) and/or in communication with the Scanner 10S (FIG. 3) obtains MR image data. The reverse operation can also be used. The circuit 60*c* can then rapidly render the resultant visualization(s) with the flexible device(s) 80 shown with a physical representation based on spatial coordinates of the devices in the 3-D imaging space identified using the associated tracking coil data and the near RT MR image(s).

Figure 3:
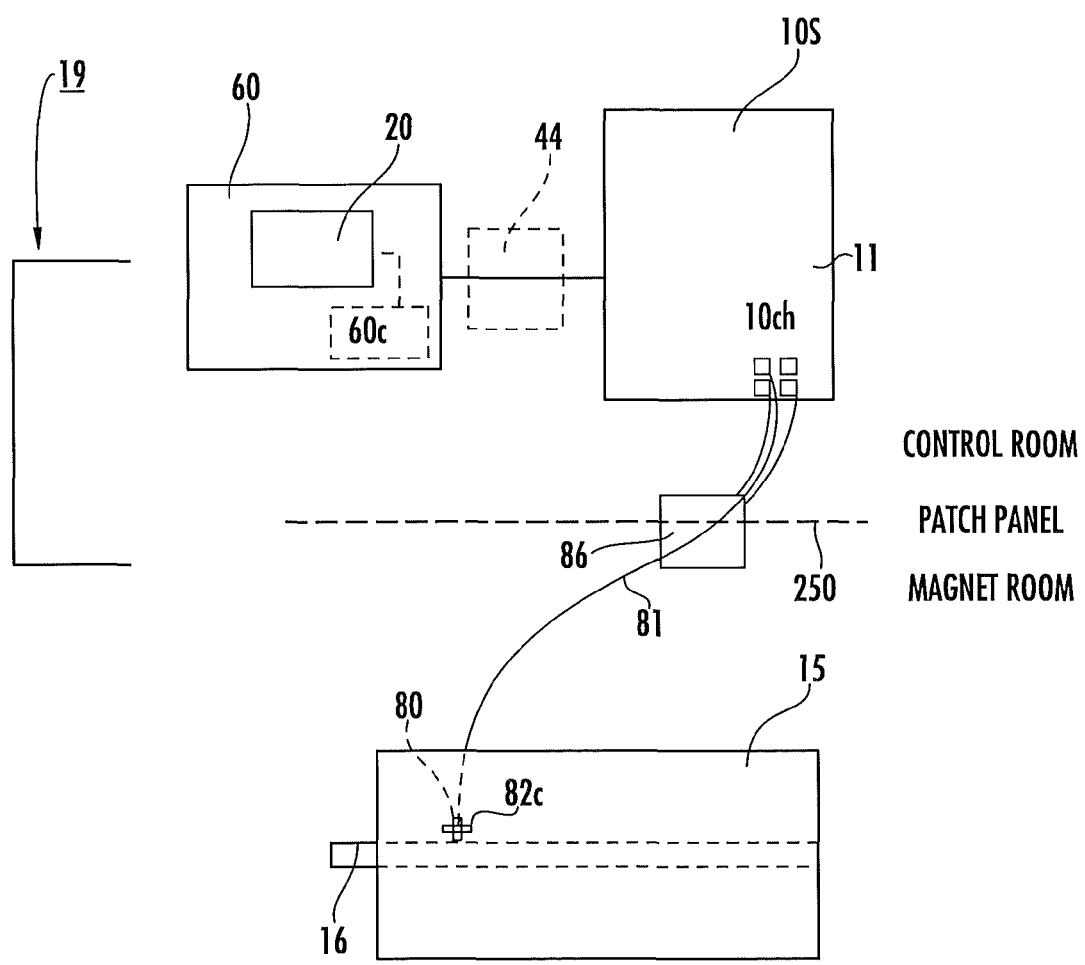
FIG. 3 is a schematic illustration of an MRI system with a workstation and display.

The circuit 60*c* can be totally integrated into the MR Scanner 10S (e.g., control cabinet), partially integrated into the MR Scanner 10S or be separate from the MR Scanner 10S but communicate therewith. If not totally integrated into the MR Scanner 10S, the circuit 60*c* may reside partially or totally in a workstation 60 and/or in remote or other local processor(s) and/or ASIC. FIG. 3 illustrates that a clinician workstation 60 can communicate with the MR Scanner 10S via an interface 44. Similarly, the device 80 in the magnet room can connect to the MR Scanner 10S via an interface box 86 which may optionally be integrated into the patch panel 250.

As shown in FIGS. 2 and 3, for example, the system 10 can include at least one (interactive) display 20 in communication with the circuit 60*c* and/or the Scanner 10S. The display 20 can be configured to display the interactive visualizations. The visualizations can be dynamic showing the movement of the device 80 relative to the intrabody anatomical structure shown by the displayed near-real time MRI image.

FIG. 2 illustrates that the device 80 can include at least one conductor 81, such as a coaxial cable that connects a respective tracking coil 82*c* to a channel 10*ch* of the MR Scanner 10S. The MR Scanner 10S can include at least 16 separate channels, and typically more channels but may operate with less as well. Each device 80 can include between about 1-10 tracking coils, typically between about 1-4. The coils 82*c* on a particular device 80 can be arranged with different numbers of turns, different dimensional spacing between adjacent coils 82*c* (where more than one coil is used) and/or other configurations. The circuit 60*c* can be configured to generate the device renderings based on tracking coil locations/positions relative to one another on a known device with a known shape and/or geometry or predictable or known changeable (deflectable) shape or form (e.g., deflectable end portion). The circuit 60*c* can identify or calculate the actual shape and orientation of the device for the renderings based on data from a CAD (computer aided design) model of the physical device. The circuit 60*c* can include data regarding known or predictable shape behavior based on forces applied to the device by the body or by internal or external components and/or based on the positions of the different tracking coils in 3-D image space and known relative (dimensional) spacings.

As shown in FIG. 3, the display 20 can be provided in or associated with a clinician workstation 60 in communication with an MRI Scanner 105. Other displays may be provided. The MRI Scanner 10S typically includes a magnet 15 in a shielded room and a control cabinet 11 (and other components) in a control room in communication with electronics in the magnet room. The MM Scanner 10S can be any MRI Scanner as is well known to those of skill in the art. A gantry 16 may be used to translate a patient in and out of the bore of the magnet 15.

Figure 4:
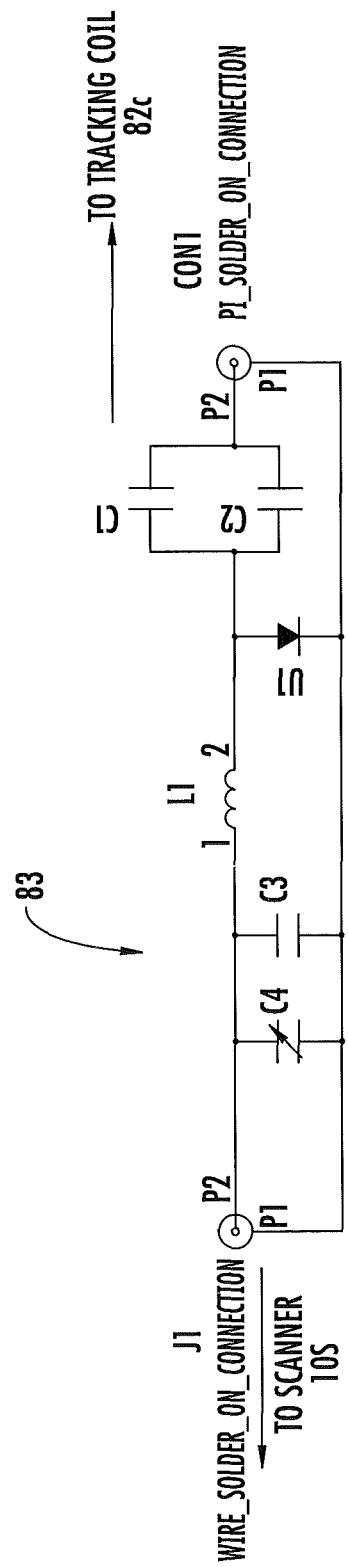
FIG. 4 is a circuit diagram of an exemplary tracking coil tuning circuit.

The tracking coils 82*c* can each include a tuning circuit that can help stabilize the tracking signal for faster system identification of spatial coordinates. FIG. 4 illustrates an example of a tuning circuit 83 that may be particularly suitable for a tracking coil 82*c*. As shown, CON1 connects the coaxial cable 81 (FIGS. 2-3) to the tracking coil 82c on a distal end portion of the device 80 while J1 connects to the MR Scanner channel 10ch (FIG. 3). The Scanner 10S sends a DC bias to the circuit 83 and turns U1 diode "ON" to create an electrical short which creates a high impedance (open circuit) on the tracking coil to prevent current flow on the tracking coil and/or better tracking signal (stability). The tuning circuit 83 can be configured to have a 50 Ohm matching circuit (narrow band to Scanner frequency) to electrically connect the cable to the respective MR Scanner channel. When the diode U1 is open, the tracking coil data can be transmitted to the MR Scanner receiver channel 10ch. The C1 and C2 capacitors are large DC blocking capacitors. C4 is optional but can allow for fine tuning (typically between about 2-12 picofarads) to account for variability (tolerance) in components. It is contemplated that other tuning circuits and/or tracking signal stabilizer configurations can be used. The tuning circuit 83 can reside in the intrabody device 80 (such as in a handle (e.g., 440, FIG. 5) or other external portion), in a connector that connects the coil 82c to the respective MRI scanner channel 10ch, in the Scanner 10S, in an interface box 86 (FIG. 2), a patch panel 250 and/or the circuit 83 can be distributed among two or more of these or other components.

In some embodiments, each tracking coil 82c can be connected to a coaxial cable 81 having a length to the diode via a proximal circuit board (which can hold the tuning circuit and/or a decoupling/matching circuit) sufficient to define a defined odd harmonic/multiple of a quarter wavelength at the operational frequency of the MRI Scanner 10S, e.g., λ/4, 3λ/4, 5λ/4, 7λ/4 at about 123.3 MHz for a 3.0 T MRI Scanner. This length may also help stabilize the tracking signal for more precise and speedy localization. The tuned RF coils can provide stable tracking signals for precise localization, typically within about 1 mm or less. Where a plurality (e.g., two closely spaced) of adjacent tracking coils are fixed on a substantially rigid material, the tuned RF tracking coils can provide a substantially constant spatial difference with respect to the corresponding tracking position signals.

Additional discussion of tracking means and ablation catheters can be found in U.S. Pat. Nos. 6,701,176 and 8,369,930, and in U.S. Patent Application Publication Nos.: 2013/0131496 and 2013/0123598, the contents of which are hereby incorporated by reference as if recited in full herein. Exemplary catheters will be discussed further below.

Figure 5:
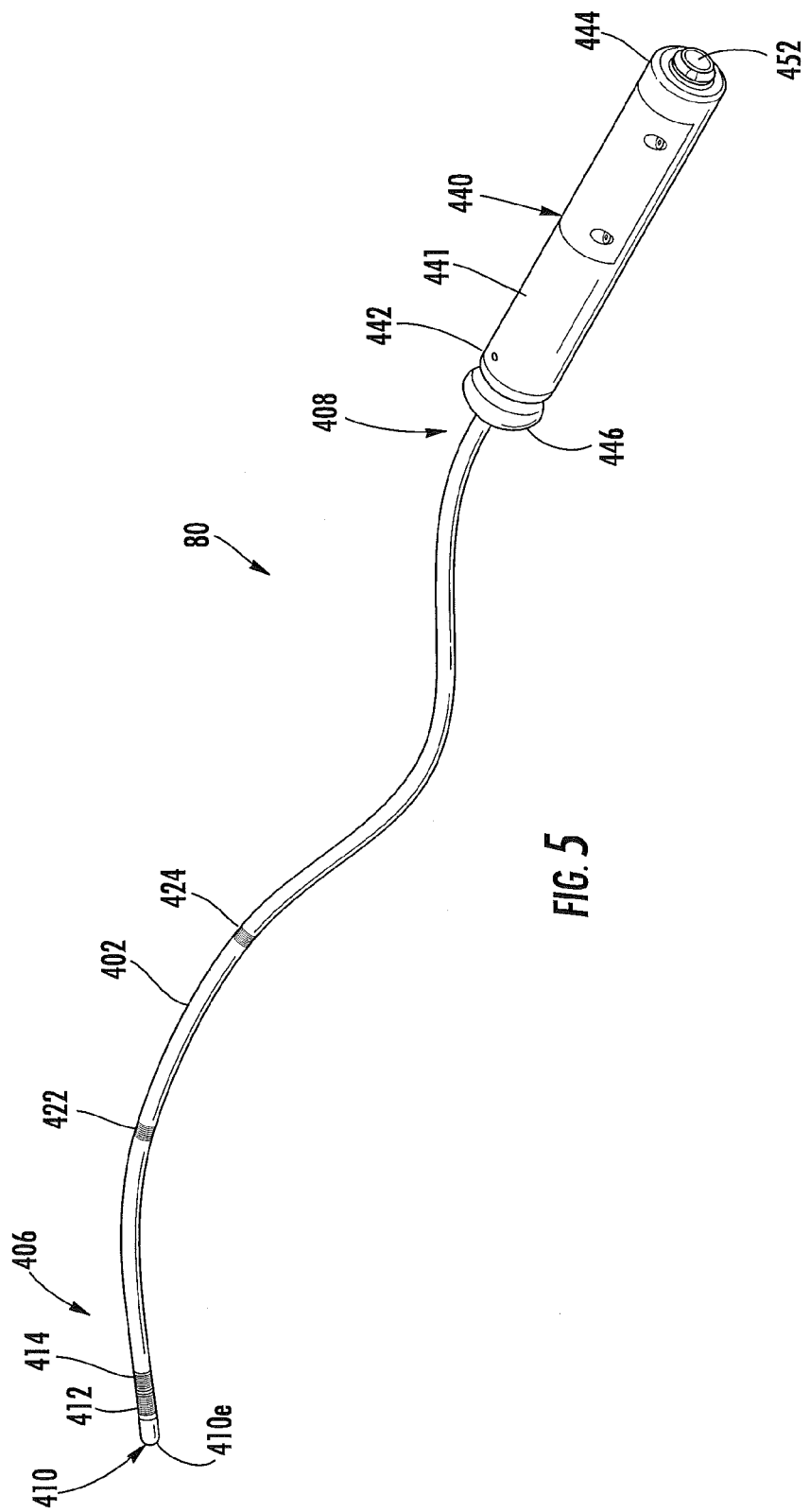
FIG. 5 is a perspective view of an exemplary ablation catheter having an ablation electrode and RF tracking coils that can be electrically connected to an interface circuit of an MRI scanner by electrical lead assemblies according to some embodiments of the present invention.

FIG. 5 illustrates a flexible (steerable) ablation catheter 80 having an ablation electrode 410e and RF tracking coils 412, 414, 422, 424 that can be electrically connected to an interface circuit 44 (FIG. 3) of an MRI scanner 10S. The illustrated ablation catheter 80 includes an elongated flexible housing or shaft 402 having at least one lumen therethrough and includes opposite distal and proximal end portions 406, 408, respectively. The distal end portion 406 includes an ablation tip 410 having an ablation electrode 410e for ablating target tissue. A pair of RF tracking coils individually identified as 412, 414, and which are functionally equivalent to coils 82c of FIGS. 2-3, are positioned upstream from the ablation tip 410, as illustrated. The RF tracking coils 412, 414 may be supported by a tip assembly 500 as described below with respect to FIGS. 6A-6B, 7 and 8. The proximal end portion 408 of the catheter 80 is operably secured to a handle 440.

However, to be clear, while the tip assembly 500 is discussed below with respect an ablation catheter, it is understood that the tip assembly 500 can be used with other intrabody medical devices. Embodiments of the present invention are not limited to ablation catheters.

Referring now to FIGS. 6A-6B, 7 and 8, a substantially rigid tip assembly 500 for a medical device, such as medical device 80 (FIGS. 1-3), is illustrated according to some embodiments of the present invention. The illustrated tip assembly 500 includes first and second tubular members 510, 520, a tip electrode 530, and a ring electrode 540. The tip assembly 500 is configured to maintain the two tracking coils 412, 414 in a fixed spatial relationship with each other and with the device tip 410 during use of the medical device 80.

Figure 6:
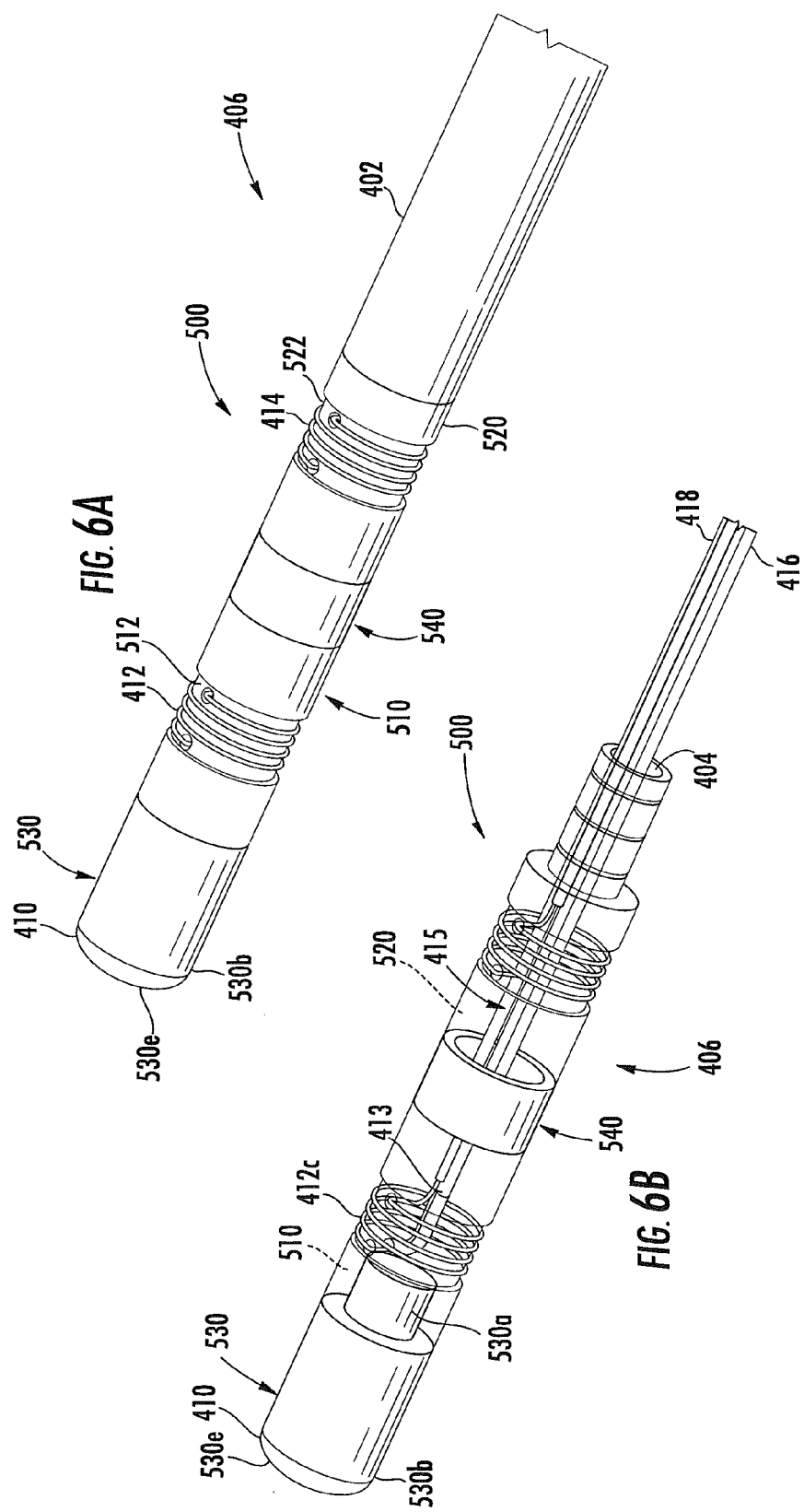
FIG. 6A is an enlarged partial perspective view of the distal end portion of the ablation catheter of FIG. 5 illustrating a tip assembly, according to some embodiments of the present invention.
FIG. 6B illustrates the ablation catheter distal end portion of FIG. 6A with some of the features of the tip assembly in phantom line.
Figure 7:
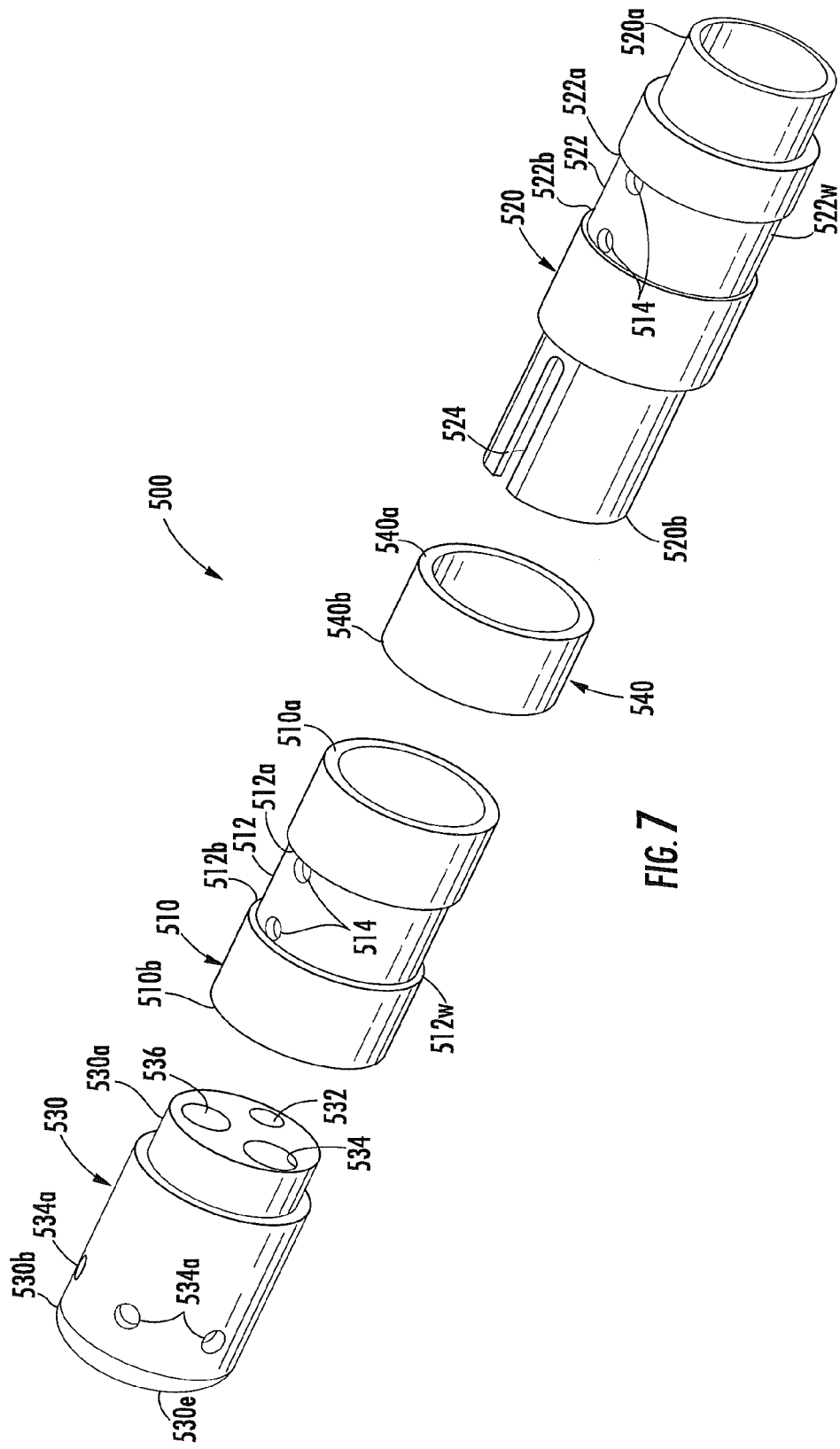
FIG. 7 is an exploded view of the tip assembly of FIG. 6A without the tracking coils.

FIG. 7 is an exploded view of the tip assembly 500 of FIGS. 6A-6B that illustrates the various components thereof. The first tubular member 510 includes opposite proximal and distal ends 510a, 510b and a circumferentially and longitudinally extending recessed portion 512 located between the proximal and distal ends 510a, 510b. The recessed portion 512 includes opposing ends 512a, 512b and a pair of apertures 514 formed through an outer wall 512w of the recessed portion 512. In the illustrated embodiment, each aperture 514 is located proximate to a respective end 512a, 512b of the recessed portion 512. The apertures 514 can be aligned as shown, or can be offset.

The second tubular member 520 includes opposite proximal and distal ends 520a, 520b and a circumferentially and longitudinally extending recessed portion 522 located between the proximal and distal ends 520a, 520b. The recessed portion 522 includes opposing ends 522a, 522b and a pair of apertures 514 formed through an outer wall 522w of the recessed portion 522. In the illustrated embodiment, each aperture 514 is located proximate to a respective end 522a, 522b of the recessed portion 522. The apertures 514 can be aligned as shown, or can be offset.

The second tubular member distal end 520b includes a longitudinally extending slot 524 formed therein, as illustrated. The slot 524 provides access for one or more conductors 415 (FIG. 6B) connected to the ring electrode 540. The slot can reside in a circumferentially and longitudinally extending recessed end or "stepped down" diameter of the second tubular member 520.

The tip electrode 530 includes opposite proximal and distal ends 530a, 530b, and the ring electrode 540 includes opposite proximal and distal ends 540a, 540b. The tip electrode proximal end 530a is adapted to be matably inserted within the first tubular member distal end 510b, and the second tubular member distal end 520b is adapted to be matably inserted through the ring electrode 540 and inserted within the first tubular member proximal end 510a. The tip electrode proximal end 530a and the first tubular member distal end 510b may be sized and configured to create frictional engagement therebetween (e.g., an interference fit) and such that the tip electrode 530 and first tubular member 510 are secured together. Similarly, the second tubular member distal end 520b and the first tubular member proximal end 510a may be sized and configured to create frictional engagement therebetween (e.g., an interference fit) and such that the first and second tubular members 510, 520 are secured together. Alternatively or in addition, an adhesive (not shown) may be utilized to secure the tip electrode proximal end 530a and the first tubular member distal end 510b together and/or the second tubular member distal end 520b and the first tubular member proximal end 510a together.

The tip electrode 530 includes an ablation electrode 530e at the distal end 530b thereof. RF power is supplied to the ablation electrode 530e via a conductor 413 (FIG. 6B) that extends through a passageway 532 formed in the tip electrode 530 beginning at the proximal end 530a thereof. The conductor extends longitudinally within a lumen (e.g., 404, FIG. 6B) in the shaft 402 to an electrical connector interface, for example, within the handle 440 (FIG. 5). The conductor connects the ablation electrode 530e to an RF generator, as would be understood by one skilled in the art. The RF ablation electrode 530e is formed from an MRI-compatible conductive material capable of receiving RF energy and ablating tissue.

The illustrated tip electrode 530 also includes an irrigation passageway 534 formed therein that terminates at a plurality of circumferentially spaced-apart apertures 534a adjacent the tip electrode distal end 530b. An irrigant fluid can be delivered to the irrigation pathway 534 from a source via a conduit (not shown) extending through a lumen in the shaft 402. The illustrated tip electrode 530 also includes a passageway 536 that is configured to house a thermistor (not shown) for measuring the temperature of tissue proximate to the ablation electrode 530e. As would be understood by one skilled in the art, a conductor extending through a lumen in the shaft 402 of the device 80 would electrically connect the thermistor to an electrical interface.

Referring back to FIGS. 6A-6B, each circumferential recessed portion 512, 522 in the first and second tubular members 510, 520 is configured to support an RF tracking coil 412, 414. The tracking coil 412 supported within recessed portion 512 of the first tubular member 510 is formed by a conductor 412c that extends outward from one aperture 514 in the first tubular member recessed portion 512, coils around the recessed portion 512, and extends inward through the other aperture 514. Similarly, the tracking coil 414 supported within recessed portion 522 of the second tubular member 520 is formed by a conductor 414c that extends outward from one aperture 514 in the second tubular member recessed portion 522, coils around the recessed portion 522, and extends inward through the other aperture 514. The illustrated tracking coils 412, 414 have four turns; however, the tracking coils 412, 414 can have various numbers of turns (typically between two and twenty turns) and/or other configurations. The illustrated tubular members 510, 520 can have different numbers of tracking coil turns or the same, as shown.

The RF tracking coils 412, 414 are each electrically connected to a respective channel of an MRI scanner 10S (FIGS. 1-3) for tracking the location of a device 80 (e.g., an ablation catheter or other type of catheter/intrabody device) in 3-D space, via respective cables (e.g., coaxial cables, twisted wire pairs, etc.) 416, 418 (FIG. 6B) extending longitudinally through the catheter shaft lumen 404 and terminating at an electrical connector interface (not shown) that is located, for example, in the handle 440 (FIG. 5).

The recessed portions 512, 522 of the first and second tubular members 510, 520 position the two RF tracking coils 412, 414 a known distance from each other and upstream from the distal end 530b of the tip electrode. Because of the fixed location of the tracking coils 412, 414 and because of the rigid nature of the tip assembly 500, the distance from either of the first and second tracking coils 412, 414 to the distal end 410 of the flexible shaft 402 can be easily determined during an MRI-guided procedure. For example, as illustrated in FIG. 8, D1 represents a known distance between the center of tracking coil 412 and the ablation electrode 530e, D2 represents a known distance between the center of tracking coil 414 and the ablation electrode 530e, and distance D3 represents a known distance between the two tracking coils 412, 414. Thus, by knowing the location of at least one of the tracking coils 412, 414 during an MRI-guided procedure, the location of the ablation electrode 530e can be easily determined. The known distances may be calculated from end to end or in other suitable ways to establish the known fixed distance relationship.

Referring to FIG. 9, a tip assembly 600 for an MRI-compatible medical device (e.g., 80, FIGS. 1-3), according to other embodiments of the present invention, is illustrated. The tip assembly 600 includes a single tubular member 610 having opposite proximal and distal ends 610a, 610b. A pair of spaced-apart circumferential recessed portions 612 are located between the proximal and distal ends 610a, 610b. Each recessed portion 612 has opposing ends 612a, 612b. A pair of apertures 614 are formed in each recessed portion 612 with each aperture 614 proximate a respective end 612a, 612b of the recessed portion 612. The apertures 614 can be aligned as shown, or can be offset.

In some embodiments, a tip electrode (530, FIG. 7) is secured to the tubular member distal end 610b. As described above, a portion of the tip electrode proximal end (530a, FIG. 7) is slidably received within the tubular member distal 610b end to secure the tip electrode 530 to the tubular member 610.

Each circumferential recessed portion 612 in the tubular member 610 is configured to support a respective RF tracking coil 412, 414. The tracking coil 412 supported within the first recessed portion 612 is formed by a conductor 412c that extends outward from one aperture 614 in the first recessed portion 612, coils around the recessed portion 612, and extends inward through the other aperture 614. Similarly, the tracking coil 414 supported within the second recessed portion 612 is formed by a conductor 414c that extends outward from one aperture 614 in the second recessed portion 612, coils around the recessed portion 612, and extends inward through the other aperture 614. The illustrated tracking coils 412, 414 have four turns; however, the tracking coils 412, 414 can have various numbers of turns (typically between two and twenty turns) and/or other configurations.

As described above, the RF tracking coils 412, 414 supported by the tip assembly 600 are each electrically connected to a respective channel of an MRI scanner 10S (FIGS. 1-3) for tracking the location of a device 80 (e.g., an ablation catheter or other type of catheter/intrabody device) in 3-D space, via respective cables (e.g., coaxial cables, twisted wire pairs, etc.) 416, 418 (FIG. 6B) extending longitudinally through the catheter shaft lumen 404 (FIG. 6B) and terminating at an electrical connector interface (not shown) that is located, for example, in the handle 440 (FIG. 5).

The first and second recessed portions 612 position the two RF tracking coils 412, 414 a known distance from each other and upstream from the distal end of a device to which the tip assembly 600 is secured, as described above with respect to FIG. 8.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An MRI-compatible medical device, comprising:
an elongated flexible shaft having a distal end portion, and an opposite proximal end portion; and
a substantially rigid tip assembly at the flexible shaft distal end portion, the tip assembly comprising:
a first tubular member comprising opposite proximal and distal ends and a circumferential recessed portion located therebetween;
a ring electrode;
a second tubular member defining an internal longitudinal passageway for receiving one or more leads therethrough, the second tubular member comprising opposite proximal and distal ends and a circumferential recessed portion located therebetween;
wherein the second tubular member distal end extends through the ring electrode and is secured to the first tubular member proximal end, wherein the second tubular member distal end comprises an outer wall with a longitudinally extending slot in communication with the internal longitudinal passageway that provides access for the one or more leads in the internal longitudinal passageway to be connected to the ring electrode.

2. The device of claim 1, further comprising a tip electrode comprising opposite proximal and distal ends, wherein the tip electrode proximal end is secured to the first tubular member distal end.

3. The device of claim 2, wherein a portion of the tip electrode proximal end is slidably received within the first tubular member distal end to secure the tip electrode to the first tubular member, and wherein a portion of the second tubular member distal end is slidably received within the first tubular member proximal end.

4. The device of claim 2, wherein the tip electrode comprises an irrigation passageway formed therein that terminates at a plurality of circumferentially spaced-apart apertures in the tip electrode.

5. The device of claim 2, wherein the tip electrode proximal end and the first tubular member distal end are sized and configured to create an interference fit therebetween.

6. The device of claim 1, wherein the second tubular member distal end and the first tubular member proximal end are sized and configured to create an interference fit therebetween.

7. The device of claim 2, wherein the tip electrode comprises an ablation electrode at the distal end thereof, and wherein RF power is supplied to the ablation electrode via a conductor that extends through a passageway formed in the tip electrode beginning at the proximal end thereof.

8. The device of claim 5, wherein the conductor extends longitudinally within a lumen in the shaft to an electrical connector interface, and wherein the conductor connects the ablation electrode to an RF generator.

9. The device of claim 1, wherein a first conductor extends outward from one aperture in the first tubular member recessed portion, coils round the first tubular member recessed portion to define a first tracking coil, and extends inward through the other aperture, and wherein a second conductor extends outward from one aperture in the second tubular member recessed portion, coils round the second tubular member recessed portion to define a second tracking coil, and extends inward through the other aperture.

10. The device of claim 9, wherein the first and second tracking coils are connected to an electrical connector interface proximate the flexible shaft proximal end portion, and wherein the electrical connector interface is configured to electrically connect the first and second tracking coils to an MRI scanner.

11. The device of claim 10, further comprising a handle attached to the flexible shaft proximal end portion, wherein the handle includes the electrical connector interface.

12. The device of claim 1, wherein each recessed portion comprises opposing ends, and wherein a pair of apertures are formed in each recessed portion, each aperture proximate a respective end of the recessed portion.

13. The device of claim 12, wherein the pair of apertures are aligned.

14. The device of claim 1, wherein an outer diameter of the first and second tubular members is the same.

15. The device of claim 9, wherein the first and second tracking coils each have between two and twenty turns.

16. The device of claim 1, wherein the second tubular member distal end comprises a length sufficient to reach the first tubular member recessed portion when inserted through the ring electrode and into the first tubular member proximal end.

* * * * *